United States Patent [19]

Mori

[11] Patent Number: 5,254,691
[45] Date of Patent: Oct. 19, 1993

[54] PHOSPHORYLATING AGENT AND METHOD FOR FORMING PHOSPHODIESTER BOND USING THE SAME

[75] Inventor: Hideto Mori, Minami-ashigara, Japan

[73] Assignee: Fuji Photo Film Co., Ltd., Kanagawa, Japan

[21] Appl. No.: 20,436

[22] Filed: Feb. 22, 1993

Related U.S. Application Data

[63] Continuation of Ser. No. 782,049, Oct. 23, 1991, abandoned.

[30] Foreign Application Priority Data

Oct. 29, 1990 [JP] Japan .................. 2-291104

[51] Int. Cl.$^5$ ................... C07F 9/28
[52] U.S. Cl. ................... 548/111; 548/113; 548/114; 548/116; 548/117; 548/118
[58] Field of Search ............ 548/111, 113, 114, 116, 548/117, 118

[56] References Cited

U.S. PATENT DOCUMENTS 4,474,947 10/1984 Hudson et al. .......... 536/27
4,476,301 10/1984 Imbach et al. .......... 536/27

FOREIGN PATENT DOCUMENTS 0064796 11/1982 European Pat. Off. .......... 536/27

OTHER PUBLICATIONS

CA 110:154782h Analogs of . . . biosynthesis. Broxterman, et al. p. 771, 1989.

Chemical Abstracts, vol. 86, No. 9, Feb. 26, 1977, Columbus, Ohio, US; Abstract No. 55668, p. 463.

Primary Examiner—Mary C. Lee
Assistant Examiner—Joseph K. McKane
Attorney, Agent, or Firm—Sughrue, Mion, Zinn, MacPeak & Seas

[57] ABSTRACT

A phosphorylating agent represented by the following general formula [1]:

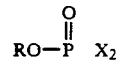

[1]

wherein R represents a protective group of the phosphoric acid; and X represents a heterocyclic residue represented by the following general formula [2]:

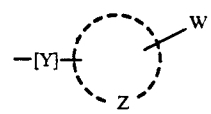

[2]

wherein Y represents a single bond or an oxygen or sulfur atom; Z represents a heterocyclic nucleus comprising at least one nitrogen atom as a ring-forming element and may be condensed with another aromatic ring; and W represents one or more substituents other than a hydrogen atom. The phosphorylating agent is stable, can rapidly proceed phosphodiester bond-forming reactions in good selectivity under mild conditions and thus makes it possible to perform a reaction even in a relatively large scale.

13 Claims, No Drawings

PHOSPHORYLATING AGENT AND METHOD FOR FORMING PHOSPHODIESTER BOND USING THE SAME

This is a continuation of application Ser. No. 07/782,049 filed Oct. 23, 1991, now abandoned.

BACKGROUND OF THE INVENTION

1. Field of the Invention

The present invention relates to a phosphorylating agent and a method for forming a phosphodiester bond using the phosphorylating agent.

2. Prior Art

The phosphodiester bond is universally present in many biomolecules such as nucleic acids, phospholipids, sugar phosphates and coensymes. These molecules are essential for organisms to manifest various functions thereof and to preserve the species by themselves. Recently, there have been actively done many attempts to imitate the excellent functions of these biomolecules and to make the most use of knowledges about organic chemistry to thereby apply them in chemical and technological fields. For this reason, it has become one of most important subjects in recent organic synthesis to synthesize molecules having a phosphodiester bond in high efficiency.

The simplest and most rational method for forming a phosphodiester bond generally comprises phosphorylating two kinds of alcohol components in order with a divalent phosphorylating agent. Phosphorylating agents often used for this purpose are chlorophosphates such as phenylphosphoric acid dichloride (see, for instance, Chemistry and Physics of Lipids, 41, 1980, p. 1). In particular, phenylphosphoric acid dichloride is presently put on the market and the method for phosphorylating two kinds of alcohols in order with the reagent has been used as a simple and reliable technique since the earliest stage of studies in this field, for example, in the synthesis of nucleic acids and phospholipids. However, this phosphorylating agent is a bifunctional reagent carrying two chlorine atoms as leaving groups and it does not show any difference in reactivity between the first and second phosphorylation reactions. For this reason, it suffers from a severe problem in that these reactions are inevitably accompanied by formation of undesirable symmetrical phosphates as by-products. For instance, this method was used in the studies of nucleic acid synthesis in the early stage, and, in 1978, Reese et al. reported the synthesis of TpT using phenylphosphoric acid dichloride, but it has been pointed out that the method likewise suffers from the problem of the formation of 3'→3' dinucleotide ester as a by-product (see Tetrahedron, 34, 1978, p. 3143).

There have been developed various methods for eliminating the foregoing problems. First, Reese et al. examined a phosphorylating agent carrying two kinds of leaving groups X and Y which differ in ability as a leaving group from one another (ability as a leaving group: X>Y), as a result found out a phosphorylating agent of the formula [3] in which one of the leaving groups is substituted with p-nitrophenoxy group and investigated the application thereof to oligonucleotide synthesis. However, it can be applied only to the step-wise synthesis and thus it is still insufficient from the viewpoint of general-purpose properties of the method (Tetrahedron Letters, 30, 1978, p. 2727)

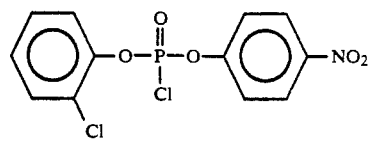

In addition, a method in which a trivalent phosphorylating agent is employed has been developed on the basis of studies of nucleic acid synthesis. This method comprises forming an internucleotide bond by the use of the high reactivity of the trivalent phosphorus atom and then oxidizing the trivalent phosphorus atom into a pentavalent phosphorus atom to form a triester compound. In the early stage of such studies, the use of phosphorochloridite in the reaction had been investigated and it was found out that an intended product can very rapidly be prepared (Tetrahedron Letters, 21, 1980, p. 719). However, this method likewise suffers from various problems that formation of the by-product, 3'→3' dinucleotide ester, is liable to occur, that the trivalent phosphorus atom is extremely unstable to moisture and that it is impossible to form any block bonding of the trivalent phosphorus atom. Therefore, this method is not practically applicable to a liquid phase method.

Then, Caruthers and his coworkers investigated the reaction in more detail and as a result, found out that morpholidite and diisopropylamidite are well applicable to the reaction (Nucleic Acid Research, 11, 1983, p. 2575; and J. Am. Chem. Soc., 105, 1983, p. 661). After the condensation reaction, the intended protected phosphoric acid triester can be obtained by oxidizing the condensate with iodine-water in a good yield. The nucleic acid synthesis through this amidite method has presently been variously improved from the viewpoint of carriers and reaction conditions and almost established as a routine work. Automatic nucleic acid synthesizers in which the reaction operations are mechanically performed have already been put on the market.

In addition, Boom et al. tried to apply this amidite method to synthesis of nucleopeptides with remarkable success (Tetrahedron, 44, 1988, p. 6515). Moreover, the phosphite method can be applied to phospholipid synthesis and there have been proposed synthesis of some phospholipids and derivatives thereof (see, for instance, Tetrahedron Letters, 29, 1988, p. 3631; and J. Org. Chem., 51, 1986, p. 2368).

However, the methods using a trivalent phosphorylating agent comprises complicated operations. For instance, the method using a chloridite requires the use of a very low reaction temperature of the order of −78° C. to suppress the formation of undesirable symmetrical by-products, while the amidite method requires the use of severe anhydrous conditions. For this reason, the phosphite method suffers from various problems if it is applied to the preparation of phospholipids in a practical scale, unlike the synthesis of nucleic acids in which it is necessary to prepare them in only a small amount.

On the other hand, there have recently been discovered a pentavalent phoshorylating agent where the phosphorus atom is activated by a substituent other than a chlorine atom and which behaves as a monofunctional agent though it is bifunctional, and it has practically been used.

First, Katagiri, Narang et al. developed phosphoroditriazolide of the formula [4] obtained by activating phosphorus atom with an azole instead of a chlorine atom and thus succeeded in the preparation of asymmetrical phosphoric acid esters without the formation of the undesirable by-product, 3'→3' dinucleotide esters (J. Am. Chem. Soc., 97, 1975, p. 7332).

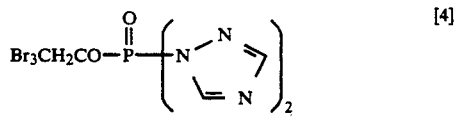
[4]

In addition, in 1981, Boom et al. proposed the use of another useful phosphorylating agent, i.e., 1-hydroxybenzotriazole (HOBt) ester of the formula [5] (Tetrahedron Letters, 22, 1981, p. 3887). According to Boom et al., this method is likewise applicable to the formation of internucleotide bonds and synthesis of phospholipids and nucleopeptides, and it is capable of providing intended products in a high yield. However, this method requires a tremendous labor to remove the released 1-hydroxybenzotriazole and thus there remains a problem of operability.

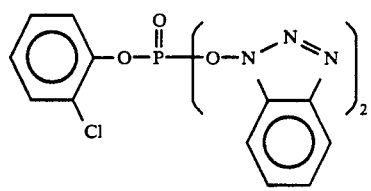
[5]

Kunieda et al. proposed the use of a phosphorylating agent of the formula [6] which is substituted with 2-oxazolone (Tetrahedron Letters, 21, 1987, p. 2375). They find out that the phosphorylation with the agent of the formula [6] is promoted by the presence of a catalytic amount of metal ions (used in the form of an acetyl acetonate) and that the activation degree varies depending on the kinds of the metals used. They succeeded in the preparation of asymmetric phosphoric acid esters by making use of the foregoing fact, i.e., by differentiating the activation degree between the first and second phosphorylation reactions. However, this method is still insufficient from the viewpoint of simplicity and practicability.

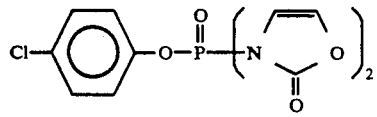
[6]

Furthermore, Ramirez et al. develop a cyclic enediol derivative of the formula [7] (they call it "Cyclic Enediol Phosphoryl (CEP) derivative") having a protective group which also serves as an activating group, and propose a method for forming asymmetric phosphodiester bonds from two different kinds of alcohols (Synthesis, 1985, p. 449).

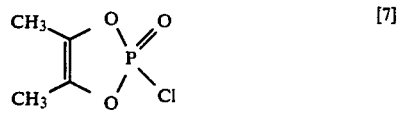
[7]

As has been discussed above, most of these conventional methods for preparing compounds carrying asymmetric phosphodiester bonds suffer from a severe problem of formation of the undesirable symmetrical by-products. Moreover, these methods require the use of strict anhydrous and/or cryogenic conditions, a tremendous labor is required for preparing necessary reagents and the resulting reagents have low storage stability. Therefore, these methods are not always practicable.

SUMMARY OF THE INVENTION

Accordingly, an object of the present invention is to provide a novel phosphorylating agent which is stable, can rapidly proceed the phosphorylation reactions in good selectivity under mild conditions and thus makes it possible to perform a reaction in a relatively large scale.

Another object of the present invention is to provide a method for forming an asymmetric phosphodiester bond which is practicaly applicable and makes it possible to isolate an intended product through the usual post-treatment after the completion of the reaction.

The foregoing objects of the present invention can effectively be achieved by providing a phosphorylating agent represented by the following general formula [1];

(1)

wherein R represents a protective group of the phosphoric acid and X represents a heterocyclic residue represented by the following general formula [2]:

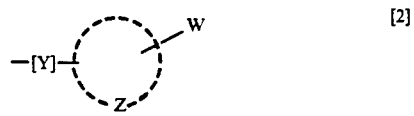
[2]

where Y represents a single bond or an oxygen or sulfur atom, Z represents a heterocyclic nucleus comprising at least one nitrogen atom as a ring-forming element, provided that it may be condensed with another aromatic ring, and W represents a substituent other than a hydrogen atom, provided that the heterocyclic residue of the formula [2] may have two or more of the substituent W; and a method for forming an asymmetric phosphodiester bond by condensing two different kinds of alcohols in order with the phosphorylating agent of the formula [1] and then removing the protective group R of the phosphoric acid.

DETAILED DESCRIPTION OF THE PREFERRED EMBODIMENTS

In the formula [1], R represents a protective group of the phosphoric acid. The term "protective group of phosphoric acid" herein means any known protective group generally used in the preparation of nucleic acids and phospholipids and specific examples thereof include aryl groups such as phenyl and o-chlorophenyl groups; alkyl groups such as methyl, 2,2,2-trichloroethyl, 2,2,2-tribromoethyl, 2-cyanoethyl and cyclopropylmethyl groups; and allyl group. The protective group may be appropriately selected from these groups while taking into consideration properties of the intended compounds and conditions for the deprotection. Particularly preferred are phenyl and methyl groups in view of easiness of obtaining a corresponding protected phosphoric acid dichloride serving as a precursor.

In the formula [1], X represents a heterocyclic residue represented by the following general formula [2];

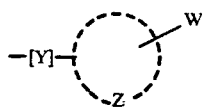

and serves as a leaving group.

In the formula [2], Y represents a single bond or a hetero atom of an oxygen or sulfur atom. Z represents a heterocyclic nucleus comprising at least one nitrogen atom as a ring-forming element, provided that it may be condensed with another aromatic ring. Examples of such nitrogen atom-containing heterocyclic rings include azoles such as imidazole, pyrazole, triazole, tetrazole, benzopyrazole, benzotriazole and pyrazolotriazole; heterocyclic rings comprising at least one nitrogen atom and other hetero atoms selected from oxygen, sulfur and/or selenium atoms such as oxazole, thiazole, benzothiazole and benzoxazole; and cyclic imides. W may be any substituent other than a hydrogen atom and it preferably ensures the formation of an HX having a pKa ranging from 3.0 to 9.0. Preferred examples of W include aromatic groups such as phenyl group; and electron attractive groups such as halogen atoms and nitro, sulfo, alkoxycarbonyl, aryloxycarbonyl, alkylsulfonyl, arylsulfonyl and cyano groups. The phenyl and alkyl moieties of the group W may have one or more substituents preferably selected from the group consisting of halogen atoms and nitro and alkoxycarbonyl groups. The compound of the formula [1] may have two or more groups of W in the heterocyclic residue of the formula [2].

In the present invention, as described above, the group X is preferably selected so that the pKa of HX, which is the conjugated acid of the releasing group X, ranges from 3.0 to 9.0. This is particularly important for the phosphorylating agent of the invention to inhibit the formation of undesirable symmetric compounds as byproducts and to exhibit proper reactivity.

The foregoing phosphorylating agent can easily be prepared by dropwise adding a solution of an HX to a solution of the corresponding phosphoric acid dichloride at room temperature in the presence of a tertiary amine such as triethylamine or pyridine. A solvent to be used may properly be selected from, for instance, tetrahydrofuran, methylene chloride and 1,4-dioxane while taking into consideration various factors such as solubility of the compounds. Although an amine hydrochloride is formed during the preparation, the reaction solution as such can usually be used in the subsequent phosphorylation reaction without removing the hydrochloride.

Specific examples of phosphorylating agents represented by Formula [1] and reactions using them will be illustrated below, but the present invention is by no means limited to those specific examples.

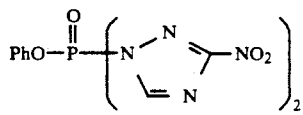

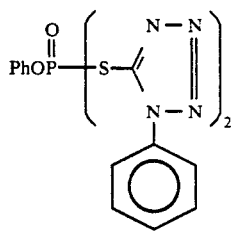

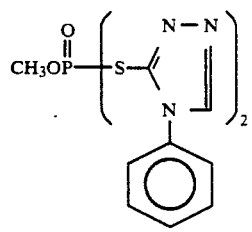

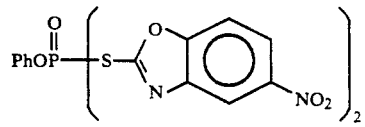

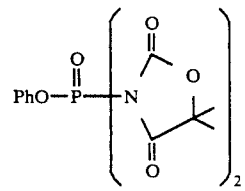

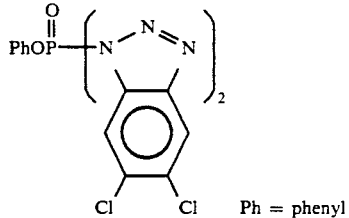

Ph = phenyl

EXAMPLES

The present invention will be explained in more detail with reference to the following non-limitative working examples.

Preparation of the Phosphorylating Agent

The phosphorylating agent of the formula [1] is generally prepared according to the following prosedures wherein a phenyl group is selected as the protective group R. However, the preparation of the phosphorylating agent is by no means limited to this preparation example.

To a solution of phenylphosphoric acid dichloride (10 mmole) in tetrahydrofuran (10 ml), there is dropwise added a solution of HX (20 mmole) and triethylamine (20 mmole) in tetrahydrofuran (20 ml) with ice cooling. The reaction solution immediately gets turbid whitely due to the formation of triethylamine hydrochloride. The reaction mixture was stirred for 30 to 60 minutes while raising the temperature thereof up to room temperature and the resulting reaction mixture as such is used in the subsequent phosphorylation.

EXAMPLE 1

Synthesis of Completely Protected Phosphatidyl Ethanolamine Derivative (R=Ph) Using the Phosphorylating Agent of the Formula [8]

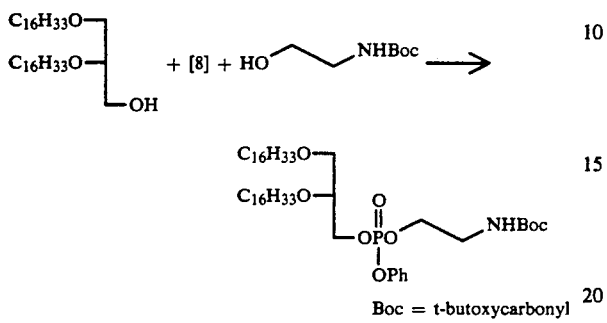

Boc = t-butoxycarbonyl

To a solution of phenylphosphoric acid dichloride (1.05 g) in tetrahydrofuran (5 ml), there was dropwise added a solution of 3-nitro-1H-1,2,4-triazole (1.14 g) and triethylamine (1.01 g) in tetrahydrofuran (10 ml) under ice cooling. The reaction mixture was stirred for 30 minutes with the temperature thereof raising to room temperature and then used in the subsequent phosphorylation.

To a solution of the agent [8] (5 mmole) prepared above in tetrahydrofuran, there was added a solution of (S)-2,3-di-O-hexadecyl-1-glycerol (2.16 g; prepared according to the method as disclosed in Biochemistry, 2, 1963, p. 394) in tetrahydrofuran (10 ml) over 10 minutes and the reaction mixture was stirred for 30 minutes at room temperature. After confirming the disappearance of the starting material by thin layer chromatography (TLC), a solution of N-t-butoxycarbonyl ethanolamine (650 mg) and N-methylimidazole (410 mg) in tetrahydrofuran (10 ml) was dropwise added to the reaction mixture. After stirring the mixture at room temperature for 30 minutes and confirming the completion of the reaction by TLC, a proper amount of water was added thereto, the organic phase was separated and the aqueous phase was extracted with ethyl acetate. After combining the organic phases and washing with water, the extract was dried over anhydrous sodium sulfate. The sodium sulfate was removed by filtration and the filtrate was concentrated under reduced pressure to give a desired product as a colorless oil. The product was solidified into a wax-like material at a low temperature.

The product was sufficiently pure without any purification and could generally be used in the subsequent process in itself, but in this Example, it was purified by silica gel chromatography (eluent: hexane/ethyl acetate=20/1 to 8/1) to give 2.8 g (yield 83.4%) of the intended product. Physicochemical properties thereof are as follows:

IR $v_{max}$ (Nujol): 3330 (m), 3060 (w), 1720 (s), 1595 (m), 1495 (s), 1280 (s), 1170 (s), 1120 (s), 1060 (sh), 1125 (s), 950 (s), 765 (m), 690 (m) cm$^{-1}$.

$^1$H-NMR δ(ppm) (200 MHz; solvent CDCl$_3$; standard substance: TMS) 0.89 (6H, deformed t, J=6 Hz), 1.28 (52H, br s), 1.44 (9H, s), 1.40–1.60 (4H, br), 3.37–3.70 (9H, m), 4.10–4.38 (4H, m), 5.00–5.18 (1H, br), 7.16–7.40 (5H, m).

FAB-MS: 862 [(M+Na)$^+$].

The protective group of the resulting completely protected phosphatidyl ethanolamine derivative could be eliminated in a conventional manner to give phosphatidyl ethanolamine having an intended asymmetric phosphodiester bond.

EXAMPLE 2

Synthesis of Completely Protected Phosphatidyl Ethanolamine Derivative (R=Ph) Using the Phosphorylating Agent of the Formula [8]

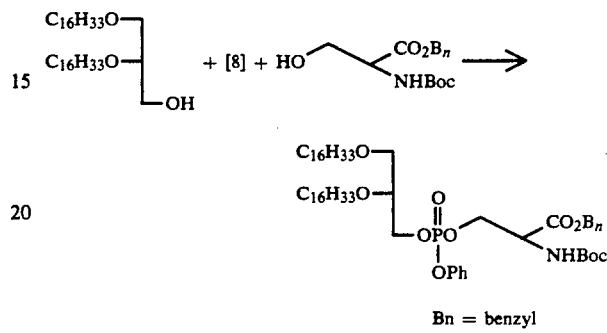

Bn = benzyl

By repeating substantially the same procedures as used in Example 1 except that (S)-N-t-butoxycarbonylserine benzyl ester (1.48 g; prepared by the method disclosed in Synthesis, 1979, p. 961) and (S)-2,3-di-O-hexadecyl-1-glycerol (2.70 g) were used, 4.09 g (yield 82%) of the desired product was obtained as colorless wax-like substance. Physicochemical properties thereof are as follows:

IR $v_{max}$ (Nujol): 3260 (m), 2930 (s), 2860 (s), 1745 (s), 1705 (s), 1600 (m), 1495 (m), 1270 (s), 1210 (s), 1165 (s), 1065 (s), 1030 (s) cm$^{-1}$.

$^1$H-NMR δ(ppm) (200 MHz; solvent CDCl$_3$; standard substance: TMS) 0.87 (6H, deformed t, J=6 Hz), 1.25 (52H, br s), 1.45 (9H, s), 1.43–1.60 (4H, br), 3.36–3.66 (7H, m), 4.05–4.30 (2H, m), 4.33–4.65 (3H, m), 5.08–5.24 (2H, m), 5.48–5.68 (1H, m), 7.11–7.40 (10H, m).

FAB MS: 974 [(M+H)$^+$].

The protective group of the resulting completely protected phosphatidyl serine derivative could be eliminated in a conventional manner to give phosphatidyl serine having an intended asymmetric phosphodiester bond.

COMPARATIVE EXAMPLE

Synthesis of Completely Protected Phosphatidyl Serine Derivative Using Phenylphosphoric Acid Dichloride To a solution of phenylphosphorodichloridate (PhO-POCl$_2$; 2.74 g; commercial product) in dry tetrahydrofuran (20 ml), there was added a solution of (S)-N-t-butoxycarbonylserine benzyl ester (2.95 g) and N-methylimidazole (1.07 g) in dry tetrahydrofuran (20 ml) over 20 minutes. After stirring the reaction mixture for 10 minutes at room temperature, a solution of (S)-2,3-di-O-hexadecyl-1-glycerol (5.4 g) and N-methylimidazole (1.07 g) in dry tetrahydrofuran (20 ml) was added to the mixture over 10 minutes and the mixture was allowed to stand at room temperature for 14 hours. The reaction solution was poured into 100 ml of water and extracted four times with 100 ml of chloroform. The organic phases were combined, washed with 150 ml of water once, and then dried over anhydrous sodium sulfate. The sodium sulfate was removed by filtration and the filtrate was concentrated under reduced pressure to give a colorless oily substance.

The crude product was purified by silica gel chromatography (eluent: hexane/ethyl acetate=20/1 to 8/1) to recover 3.41 g (yield 35%) of the desired product as a colorless wax-like substance.

The physicochemical properties of the resulting product were completely consistent with those described in Example 2.

EXAMPLE 3

Synthesis of Completely Protected Phosphatidyl Ethanolamine Derivative Using Phenylphosphoric Acid Ditriazolide

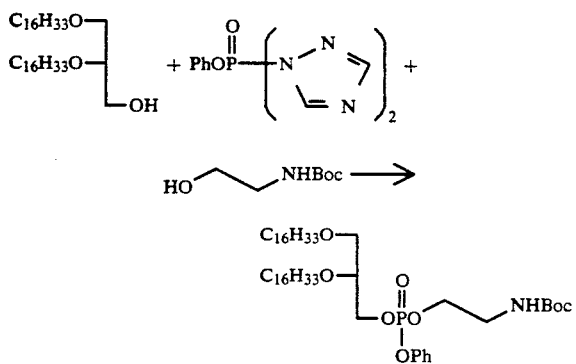

To a solution of phenylphosphoric acid dichloride (1.05 g) in tetrahydrofuran (10 ml), there was dropwise added a solution of 1H-1,2,4-triazole (690 mg) and triethylamine (1.01 g) in tetrahydrofuran (10 ml) with ice cooling. The reaction solution immediately got turbid whitely due to the formation of triethylamine hydrochloride. The reaction mixture was stirred for 30 minutes with the temperature thereof raising up to room temperature and then used in the subsequent phosphorylation.

To the solution of the phosphorylating agent thus prepared in tetrahydrofuran, there was added a solution of (S)-2,3-di-O-hexadecyl-1-glycerol (2.16 g) in tetrahydrofuran (10 ml) over 10 minutes and the reaction mixture was stirred at room temperature for 6 hours. After confirming the disappearance of the starting materials by TLC, a solution of N-t-butoxycarbonyl ethanolamine (650 mg) and N-methylimidazole (410 mg) in tetrahydrofuran (10 ml) wa added to the reaction mixture and the mixture was stirred at room temperature till the reaction was completed (15 hours). The reaction solution was subjected to substantially the same post-treatment and purification as used in Example 1 to give 2.11 g (yield 63%) of the desired product as a colorless wax-like substance.

The physicochemical properties of the resulting product were completely consistent with those described in Example 1.

EXAMPLES 4 TO 10

The phosphorylation reaction was carried out by using a variety of phosphorylating agents of the invention shown in Table 1 below. Yields of the resulting products are also summarized in Table 1. In these reactions, substantially the same procedures as used in Examples 1 and 2 were repeated.

TABLE 1

$$\text{PhOPX}_2 \xrightarrow[\text{2) R}^2\text{—OH}]{\text{1) R}^1\text{—OH}} R^1O-\overset{\overset{O}{\|}}{\underset{OPh}{P}}-OR^2$$

| Phosphorylating agent | $R^1$—OH (Reaction time) | $R^2$—OH (Reaction time) | Yield (%) |
|---|---|---|---|
| Comparative Example<br>PhOPCl$_2$ | HO–CH$_2$–CH(CO$_2$B$_n$)–NHBoc<br>(10 minutes) | C$_{16}$H$_{33}$O–, C$_{16}$H$_{33}$O–, –OH<br>(14 hours) | 35.0 |
| Example 1<br>[8]* | C$_{16}$H$_{33}$O–, C$_{16}$H$_{33}$O–, –OH<br>(30 minutes) | HO–CH$_2$–CH$_2$–NHBoc<br>(30 minutes) | 83.4 |
| Example 2<br>[8]* | C$_{16}$H$_{33}$O–, C$_{16}$H$_{33}$O–, –OH<br>(30 minutes) | HO–CH$_2$–CH(CO$_2$B$_n$)–NHBoc<br>(30 minutes) | 82.0 |
| Example 3<br>PhOP(O)(–N(triazole))$_2$ | C$_{16}$H$_{33}$O–, C$_{16}$H$_{33}$O–, –OH<br>(6 hours) | HO–CH$_2$–CH$_2$–NHBoc<br>(15 hours) | 63.0 |

TABLE 1-continued $$PhOPX_2 \xrightarrow[\text{2) } R^2-OH]{\text{1) } R^1-OH} R^1O-\underset{\underset{OPh}{|}}{\overset{\overset{O}{\|}}{P}}-OR^2$$

| Phosphorylating agent | R¹—OH (Reaction time) | R²—OH (Reaction time) | Yield (%) |
|---|---|---|---|
| Example 4 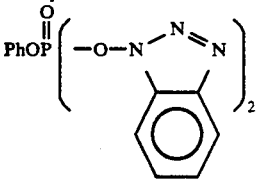 | C₁₆H₃₃O—, C₁₆H₃₃O—, —OH (5 hours) | HO⌒NHBoc (16 hours) | 77.0 |
| Example 5 [8]* | n-C₁₆H₃₃OH (20 minutes) | 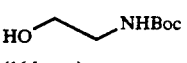 (40 minutes) | 81.6 |
| Example 6 [9]* | C₁₆H₃₃O—, C₁₆H₃₃O—, —OH (20 minutes) | HO⌒NHBoc (30 minutes) | 79.3 |
| Example 7 [10]* | C₁₆H₃₃O—, C₁₆H₃₃O—, —OH (40 minutes) | HO⌒NHBoc (1 hours) | 78.1 |
| Example 8 [11]* | C₁₆H₃₃O—, C₁₆H₃₃O—, —OH (30 minutes) | HO⌒NHBoc (1.5 hours) | 70.3 |
| Example 9 [12]* | n-C₁₆H₃₃OH (1 hours) | HO⌒NHBoc (3 hours) | 68.2 |
| Example 10 [13]* | C₁₆H₃₃O—, C₁₆H₃₃O—, —OH (40 minutes) | HO⌒NHBoc (2 hours) | 77.2 |

*Formula number
**DMTr = 4,4'-dimethoxytrityl group
B = Benzoyladenine

The compound of the present invention is a phosphorylating agent useful for forming an asymmetric phosphoric acid diester from two different kinds of alcohols in good selectivity. This phosphorylating agent can easily be prepared by reacting a corresponding phosphoric acid dichloride with HX such as 3-nitro-1,2,4-triazole and 1-phenyl-5-mercapto-1H-tetrazole at room temperature in the presence of a tertiary amine such as triethylamine or pyridine in a proper solvent. This operation is very simple and does not require the use of extremely low reaction temperature and/or strict anhydrous conditions. Further, as seen from Examples, the two-stage phosphorylation reaction rapidly proceeds and is not accompanied by any formation of an undesirable symmetric by-product. Therefore, the reaction proceeds in good yield and accordingly any purification operation such as chromatography is generally unnecessary. In addition, the reaction may be carried out easily since 3-nitro-1,2,4-triazole or the like serving as a leaving group can easily be removed by simply washing with water. As has been explained above, the compound and the method of the present invention are extremely advantageous in that the compound and the method make it possible to perform clean and large-scale phosphorylation reactions.

What is claimed is:

1. A phosphorylating agent represented by the following general formula (1):

$$RO-\overset{O}{\underset{\|}{P}}(-X)_2 \quad (1)$$

wherein R represents a protective group for phosphoric acid; and X represents a heterocyclic residue represented by the following general formula (2):

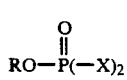  (2)

wherein Y represents a single bond, an oxygen or a sulfur atom; Z represents a heterocyclic nucleus comprising at least one nitrogen atom as a ring-forming element which may be condensed with another aromatic ring; and W is selected from the group consisting of halogen atoms and phenyl, nitro, sulfo, alkoxycarbonyl, aryloxycarbonyl, alkylsulfonyl, arylsulfonyl and cyano groups, provided that the heterocyclic residue of the formula (2) may have two or more W groups as substituents; wherein the nitrogen atom-containing heterocyclic ring is an azole ring, a heterocyclic ring comprising at least one nitrogen atom and other hetero atoms selected from oxygen, sulfur and selenium atoms or a cyclic imide.

2. The phosphorylating agent of claim 1, wherein said phosphorylating agent is:

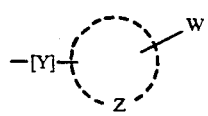

3. The phosphorylating agent of claim 1, wherein said phosphorylating agent is:

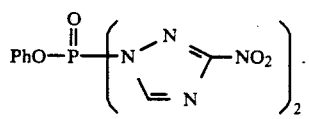

4. The phosphorylating agent of claim 1, wherein said phosphorylating agent is:

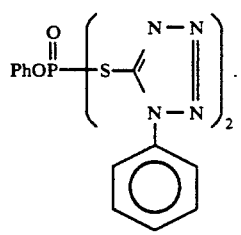

5. The phosphorylating agent of claim 1, wherein said phosphorylating agent is:

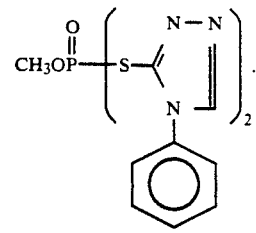

6. The phosphorylating agent of claim 1, wherein said phosphorylating agent is:

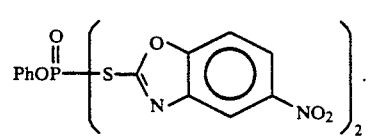

7. The phosphorylating agent of claim 1, wherein said phosphorylating agent is:

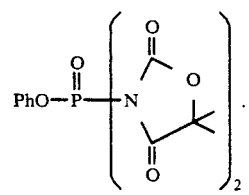

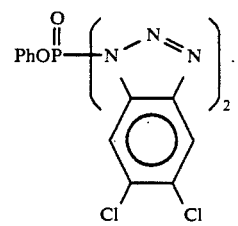

8. The phosphorylating agent of claim 1, wherein the protective group R is selected from the group consisting of aryl, alkyl and allyl group.

9. The phosphorylating agent of claim 8, wherein the protective groups R is selected from the group consisting of phenyl, o-chlorophenyl, methyl, 2,2,2-trichloroethyl, 2,2,2-tribromoethyl, 2-cyanoethyl, cyclopropylmethyl and allyl groups.

10. The phosphorylating agent of claim 9, wherein the protective group R is a phenyl or methyl group.

11. The phosphorylating agent of claim 1, wherein the nitrogen atom-containing heterocyclic ring is selected from the group consisting of imidazole, pyrazole, triazole, tetrazole, benzopyrazole, benzotriazole, pyrazolotriazole, oxazole, thiazole, benzothiazole, benzoxazole and cyclic imides.

12. The phosphorylating agent of claim 1, wherein the phenyl group and the alkyl moieties of the substituent W are substituted with a halogen atom, a nitro group and/or an alkoxycarbonyl group.

13. The phosphorylating agent of claim 1, wherein pKa of a conjugated acid of X, HX, ranges from 3.0 to 9.0.

* * * * *